(12) United States Patent
Mihori

(10) Patent No.: US 7,722,602 B2
(45) Date of Patent: May 25, 2010

(54) ELECTROSURGICAL DEVICE

(75) Inventor: Takashi Mihori, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 872 days.

(21) Appl. No.: 11/586,266

(22) Filed: Oct. 25, 2006

(65) Prior Publication Data

US 2007/0118102 A1 May 24, 2007

(30) Foreign Application Priority Data

Nov. 18, 2005 (JP) ............................. 2005-334666

(51) Int. Cl.
*A61B 18/18* (2006.01)
(52) U.S. Cl. .............................. 606/34; 606/37; 606/39; 606/40
(58) Field of Classification Search ............. 606/34–35, 606/38
See application file for complete search history.

(56) References Cited

U.S. PATENT DOCUMENTS

| 4,580,562 | A | | 4/1986 | Goof et al. |
| 5,188,122 | A | * | 2/1993 | Phipps et al. ............... 607/138 |
| 5,647,869 | A | * | 7/1997 | Goble et al. .................. 606/37 |
| 5,807,392 | A | * | 9/1998 | Eggers ......................... 606/31 |
| 6,582,427 | B1 | * | 6/2003 | Goble et al. .................. 606/37 |
| 2005/0096681 | A1 | * | 5/2005 | Desinger et al. ............ 606/169 |
| 2005/0234442 | A1 | * | 10/2005 | Spears ......................... 606/39 |

FOREIGN PATENT DOCUMENTS

| DE | 31 51 991 A1 | 1/1981 |
| JP | 10-118093 | 5/1998 |

\* cited by examiner

*Primary Examiner*—Lee S Cohen
*Assistant Examiner*—Jaymi Della
(74) *Attorney, Agent, or Firm*—Scully, Scott, Murphy & Presser, P.C.

(57) ABSTRACT

An electrosurgical device is provided which can prevent the decrease of the effect of a treatment performed by an operator or the like on a biological tissue. A high-frequency voltage generated in an alternating power supply is transformed in a transformer. A high-frequency current in accordance with the transformed high-frequency voltage is supplied to the biological tissue via two high-frequency current supply lines. In this case, the impedance between the two high-frequency current supply lines is set in an impedance matching circuit so as to become maximum with respect to the frequency of the high-frequency current. Accordingly, the decrease of the effect of the treatment performed on the biological tissue can be prevented.

11 Claims, 1 Drawing Sheet

ELECTROSURGICAL DEVICE

The present application claims priority on the basis of Japanese Patent Application No. 2005-334666 filed in Japan on Nov. 18, 2005, and the following disclosed content is cited in the specification, the claims, and the drawings of the present application.

BACKGROUND OF THE INVENTION

1. Field of the Invention

The present invention relates to an electrosurgical device capable of performing a treatment on a biological tissue with a high-frequency current.

2. Description of the Related Art

Conventionally, an electrosurgical device, such as an electric scalpel, has been used in a surgical operation or the like to perform such treatments as cutting, coagulation, and hemostasis of a biological tissue. Generally, the above-described electrosurgical device is configured to include a high-frequency power supply for outputting a high-frequency current, and a treatment tool connected to the high-frequency power supply. Through the treatment tool made in contact with a biological tissue of a patient, an operator or the like supplies the biological tissue with the high-frequency current output from the high-frequency power supply to thereby perform each of the above-described treatments on the biological tissue.

Further, it is desirable that the above-described electrosurgical device is configured to be able to supply the high-frequency current in accordance with the condition of the biological tissue to be treated or the treatment performed by the operator or the like. As a device approximately similar in configuration to the electrosurgical device having the above configuration, a high-frequency current curing device proposed in Japanese Unexamined Patent Application Publication No. 10-118093, for example, has been widely known.

SUMMARY OF THE INVENTION

An electrosurgical device according to the present invention is characterized by including: an alternating power supply for generating a high-frequency voltage; a transformer for transforming the high-frequency voltage applied to a primary circuit and outputting a high-frequency current based on the transformed high-frequency voltage from a secondary circuit; a bipolar-type treatment tool having two high-frequency current supply lines and supplying the high-frequency current output from the transformer to a biological tissue via the two high-frequency current supply lines; and an impedance matching circuit configured to have a predetermined constant which is set, on the basis of the coupling capacitance between the two high-frequency current supply lines and the frequency of the high-frequency current, such that the impedance between the two high-frequency current supply lines becomes maximum with respect to the frequency.

DETAILED DESCRIPTION OF THE PREFERRED EMBODIMENTS

Figure 1:
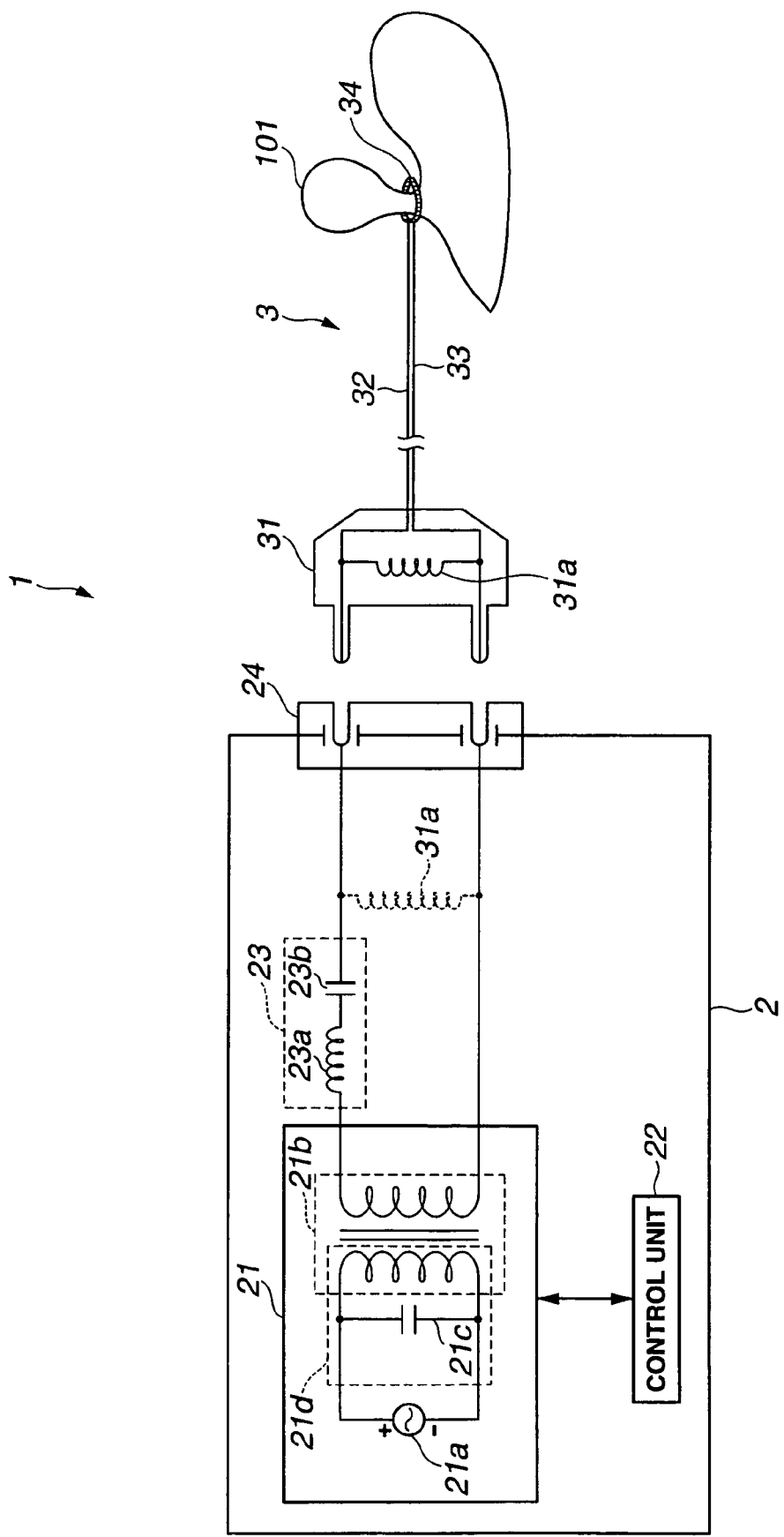
FIG. 1 is a diagram illustrating an example of a configuration of main parts of an electrosurgical device according to an embodiment.

An embodiment of the present invention will be described below with reference to the drawing. FIG. 1 is a diagram illustrating an example of a configuration of main parts of an electrosurgical device according to the present embodiment.

As illustrated in FIG. 1, major parts of an electrosurgical device 1 include a high-frequency power supply device 2 which outputs a high-frequency current, and a bipolar-type treatment tool 3 which is configured to be connectable, at the proximal end side thereof, to the high-frequency power supply device 2, and which supplies, from the distal end side thereof, the high-frequency current output from the high-frequency power supply device 2 to a biological tissue 101.

The high-frequency power supply device 2 is configured to include a high-frequency current generation unit 21, a control unit 22, a series resonance unit 23, and a bipolar socket 24 connectable to a bipolar connector 31 provided to the basal end side of the bipolar-type treatment tool 3. Further, the high-frequency current generation unit 21 is configured to include an alternating power supply 21a for outputting an alternating voltage and an alternating current, a high-frequency transformer 21b, and a capacitor 21c.

The alternating supply 21a applies a high-frequency voltage V1 having a frequency of approximately a few hundred kHz, for example, as a predetermined frequency to a primary circuit of the high-frequency transformer 21b and the capacitor 21c.

When the high-frequency voltage V1 having the predetermined frequency is applied to the primary circuit, the high-frequency transformer 21b, which serves as a transformer, causes a secondary circuit to generate a high-frequency voltage V2 having the predetermined frequency through electromagnetic induction. Then, when the high-frequency voltage V2 having the predetermined frequency is generated in the secondary circuit of the high-frequency transformer 21b, a high-frequency current based on the high-frequency voltage V2 and having the predetermined frequency is output to the bipolar socket 24 via the series resonance unit 23.

Together with a coil of the primary circuit of the high-frequency transformer 21b, the capacitor 21c forms a parallel resonance unit 21d, and the parallel resonance unit 21d performs spurious removal of the high-frequency voltage V1.

The control unit 22 formed by a CPU and the like performs a control on the high-frequency current generation unit 21, and also performs a control on each of not-illustrated parts other than the high-frequency current generation unit 21 provided in the high-frequency power supply device 2.

The series resonance unit 23 is configured to include a coil 23a and a capacitor 23b, and decreases the output impedance in the secondary circuit of the high-frequency transformer 21b.

The bipolar-type treatment tool 3 is configured to include the bipolar connector 31, a coil 31a, output lead wires 32 and 33 serving as high-frequency current supply lines for transmitting the high-frequency current output from the high-frequency power supply device 2 to a distal end portion of the bipolar-type treatment tool 3, and an insulation portion 34 provided to the distal end portion of the bipolar-type treatment tool 3 so as to prevent the short circuit between the output lead wires 32 and 33.

The bipolar connector 31 is configured to be connectable to the bipolar socket 24 of the high-frequency power supply device 2 and to include therein the coil 31a.

The coil 31a, which serves as an impedance matching circuit, is connected in parallel to the output lead wires 32 and 33 to form a parallel resonance circuit together with a coupling capacitance existing between the output lead wires 32 and 33. Further, the inductance of the coil 31a as a predetermined constant is appropriately set in accordance with the coupling capacitance existing between the output lead wires 32 and 33 and the resonance frequency based on the frequency of the high-frequency current output from the secondary circuit of the high-frequency transformer 21b included in the high-frequency power supply device 2.

The coil 31a is not limited to the one provided inside the bipolar connector 31, as long as the coil 31a is connected in parallel to the output lead wires 32 and 33 in the secondary circuit of the high-frequency transformer 21b, and as long as the inductance as the predetermined constant is appropriately set in accordance with the coupling capacitance existing between the output lead wires 32 and 33 and the resonance frequency based on the frequency of the high-frequency current output from the secondary circuit of the high-frequency transformer 21b included in the high-frequency power supply device 2. Specifically, the coil 31a may be provided, for example, between the bipolar socket 24 and the series resonance unit 23, which is located inside the high-frequency power supply device 2 and forms the secondary circuit of the high-frequency transformer 21b, as indicated by a dotted line in FIG. 1. Further, a plurality of the coils 31a may be provided inside the high-frequency power supply device 2, and a predetermined coil suitable for a treatment tool may be selected out of the plurality of the coils in accordance with such factors as the identification information specific to the treatment tool connected to the high-frequency power supply device 2, for example, to be connected to the output lead wires 32 and 33.

The operation of the electrosurgical device 1 will be then described.

The operator or the like first connects the bipolar-type treatment tool 3 to the high-frequency power supply device 2, and then turns on the power supply of the high-frequency power supply device 2.

Upon turn-on of the power supply of the high-frequency power supply device 2, the control unit 22 performs a control on the high-frequency current generation unit 21 for outputting a high-frequency current. Then, on the basis of the control by the control unit 22, the high-frequency current generation unit 21 causes the secondary circuit of the high-frequency transformer 21b to generate a high-frequency current having a frequency of approximately a few hundred kHz, for example, as a predetermined frequency.

The high-frequency current generated in the secondary circuit of the high-frequency transformer 21b is supplied from the distal end portion of the bipolar-type treatment tool 3 to the biological tissue 101 via the bipolar socket 24, the bipolar connector 31, and the output lead wires 32 and 33.

In an early stage of the supply of the high-frequency current to the biological tissue 101 from the distal end portion of the bipolar-type treatment tool 3, the impedance of the biological tissue 101 is low due to the adhesion of mucus or the like to such an extent that the reactance caused by the coupling capacitance between the output lead wires 32 and 33 can be ignored. That is, in the early stage of the supply of the high-frequency current to the biological tissue 101 from the distal end portion of the bipolar-type treatment tool 3, a pure resistance component becomes dominant among respective components of the impedance of the biological tissue 101.

Thereafter, as the high-frequency current continues to be supplied to the biological tissue 101 from the distal end portion of the bipolar-type treatment tool 3, the biological tissue 101 is gradually dried. Accordingly, the impedance of the biological tissue 101 increases to such an extent that the reactance caused by the coupling capacitance between the output lead wires 32 and 33 cannot be ignored.

Conventionally, therefore, as the high-frequency current continues to be supplied to the biological tissue 101 from the distal end portion of the bipolar-type treatment tool 3, there arises, for example, a phenomenon in which the amount of the current supplied to the biological tissue 101 gradually decreases and the amount of the current flowing via the coupling capacitance between the output lead wires 32 and 33 gradually increases.

The bipolar-type treatment tool 3 according to the present embodiment, however, includes the coil 31a whose inductance as a predetermined constant is appropriately set in accordance with the resonance frequency based on the frequency of the high-frequency current output from the high-frequency power supply device 2 and the coupling capacitance existing between the output lead wires 32 and 33. Therefore, the impedance between the output lead wires 32 and 33 becomes maximum with respect to the frequency of the high-frequency current output from the high-frequency power supply device 2. Further, since the bipolar-type treatment tool 3 includes the coil 31a, it is possible to eliminate the phase difference between the impedance of the biological tissue 101 and the reactance caused by the coupling capacitance between the output lead wires 32 and 33, which occurs when the high-frequency current continues to be supplied to the biological tissue 101 from the distal end portion of the bipolar-type treatment tool 3.

Thus, according to the above-described function of the coil 31a, even if the impedance of the biological tissue 101 has increased to such an extent that the reactance caused by the coupling capacitance between the output lead wires 32 and 33 cannot be ignored, a current does not flow via the coupling capacitance between the output lead wires 32 and 33, and the amount of the current supplied to the biological tissue 101 does not decrease.

As described above, the electrosurgical device 1 according to the present embodiment can appropriately supply the biological tissue 101 with the high-frequency current required for the treatment on the biological tissue 101, without making the high-frequency current divided via the coupling capacitance between the output lead wires 32 and 33 in the bipolar-type treatment tool 3. As a result, the electrosurgical device 1 according to the present embodiment can prevent the decrease of the effect of the treatment performed by the operator or the like on the biological tissue.

Needless to day, the present invention is not limited to the embodiment described above, but various modifications and applications can be made in the present invention within a scope not departing from the gist of the invention.

What is claimed is:

1. An electrosurgical device comprising:
    an alternating power supply for generating a high-frequency voltage;
    a transformer for transforming the high-frequency voltage applied to a primary circuit and outputting a high-frequency current based on the transformed high-frequency voltage from a secondary circuit;
    a bipolar-type treatment tool having two high-frequency current supply lines and supplying the high-frequency current output from the transformer to a biological tissue via the two high-frequency current supply lines; and
    an impedance matching circuit configured to have a predetermined constant which is set, on the basis of the coupling capacitance between the two high-frequency current supply lines and the frequency of the high-frequency current, such that the impedance between the two high-frequency current supply lines becomes maximum with respect to the frequency.

2. The electrosurgical device according to claim 1, wherein the impedance matching circuit is provided to the secondary circuit of the transformer.

3. The electrosurgical device according to claim 1, wherein the impedance matching circuit is provided inside a a connector of the bipolar-type treatment tool.

4. The electrosurgical device according to claim 2, wherein the impedance matching circuit is provided inside a connector of the bipolar-type treatment tool.

5. The electrosurgical device according to claim 1, wherein the impedance matching circuit is formed by a single coil.

6. The electrosurgical device according to claim 5, wherein the single coil is connected in parallel to the two high-frequency current supply lines.

7. The electrosurgical device according to claim 1, wherein the predetermined constant represents the inductance.

8. The electrosurgical device according to claim 5, wherein the predetermined constant represents the inductance.

9. The electrosurgical device according to claim 6, wherein the predetermined constant represents the inductance.

10. The electrosurgical device according to claim 1, wherein a high-frequency power supply device incorporates the alternating power supply and the transformer, and further includes the impedance matching circuit in the secondary circuit.

11. The electrosurgical device according to claim 1, wherein a high-frequency power supply device incorporates the alternating power supply and the transformer, and further includes a plurality of the impedance matching circuit, the high-frequency power supply device being configured for selecting one of the plurality of impedance matching circuits in accordance with the bipolar-type treatment tool to be connected to the high-frequency power supply device.

* * * * *